US012329379B2

(12) United States Patent
Shelton, IV et al.

(10) Patent No.: US 12,329,379 B2
(45) Date of Patent: Jun. 17, 2025

(54) SURGICAL SYSTEM WITH WIRELESS ARRAY FOR POWER AND DATA TRANSFER

(71) Applicant: Cilag GmbH International, Zug (CH)

(72) Inventors: Frederick E. Shelton, IV, Hillsboro, OH (US); Shane R. Adams, Lebanon, OH (US); Kevin M. Fiebig, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/379,781

(22) Filed: Oct. 13, 2023

(65) Prior Publication Data

US 2025/0120699 A1    Apr. 17, 2025

(51) Int. Cl.
*A61B 17/072* (2006.01)
*A61B 17/00* (2006.01)
*A61B 90/00* (2016.01)

(52) U.S. Cl.
CPC .. *A61B 17/072* (2013.01); *A61B 2017/00221* (2013.01); *A61B 2017/0053* (2013.01); *A61B 2017/07271* (2013.01); *A61B 2090/0808* (2016.02)

(58) Field of Classification Search
CPC .......... A61B 17/072; A61B 2090/0808; A61B 2017/00221; A61B 2017/0053; A61B 2017/07271
USPC ..................................................... 227/176.1
See application file for complete search history.

(56) References Cited

U.S. PATENT DOCUMENTS

| | | | |
|---|---|---|---|
| 7,980,443 B2 | 7/2011 | Scheib et al. |
| 8,393,514 B2 | 3/2013 | Shelton, IV et al. |
| 8,561,870 B2 | 10/2013 | Baxter, III et al. |
| 8,733,613 B2 | 5/2014 | Huitema et al. |
| 9,005,199 B2 | 4/2015 | Beckman et al. |
| 9,072,535 B2 | 7/2015 | Shelton, IV et al. |
| 9,629,629 B2 | 4/2017 | Leimbach et al. |
| 9,931,118 B2 | 4/2018 | Shelton, IV et al. |
| 10,085,749 B2 | 10/2018 | Cappola et al. |
| 11,229,437 B2 | 1/2022 | Shelton, IV et al. |
| 11,246,678 B2 | 2/2022 | Shelton, IV et al. |
| 11,903,582 B2 | 2/2024 | Baxter, III et al. |
| 11,903,587 B2 | 2/2024 | Shelton, IV et al. |
| 11,963,681 B2 | 4/2024 | Rector et al. |

(Continued)

*Primary Examiner* — Chinyere J Rushing-Tucker

(57) ABSTRACT

A surgical instrument comprises a shaft and an end effector extending from the shaft, the end effector comprising a staple cartridge comprising: a cartridge deck, a cartridge body, and a cartridge antenna supported by the cartridge body; a longitudinal channel, comprising: a base, a first wall extending from the base, a second wall extending from the base, wherein the second wall is spaced apart from the first wall to accommodate the staple cartridge therebetween in an assembled configuration, and a channel antenna supported by the first wall, wherein the cartridge antenna and the channel antenna are to cooperatively define a wireless signal-transfer circuit in the assembled configuration; and an aligner to interlock the staple cartridge and the longitudinal channel in the assembled configuration, wherein the aligner is adjacent the channel antenna and the staple cartridge antenna to maintain a predefined spatial relation between the channel antenna and the cartridge antenna in the assembled configuration.

20 Claims, 9 Drawing Sheets

(56) References Cited

U.S. PATENT DOCUMENTS

| | | | |
|---|---|---|---|
| 2014/0252065 A1* | 9/2014 | Hessler | A61B 17/0682 227/176.1 |
| 2020/0405415 A1 | 12/2020 | Shelton, IV et al. | |
| 2022/0104813 A1* | 4/2022 | Shelton, IV | A61B 17/072 |
| 2022/0104822 A1* | 4/2022 | Shelton, IV | A61B 90/92 |
| 2022/0273306 A1 | 9/2022 | Shelton, IV et al. | |
| 2022/0304680 A1* | 9/2022 | Shelton, IV | A61B 17/07207 |
| 2023/0293172 A1 | 9/2023 | Fiebig et al. | |

\* cited by examiner

SURGICAL SYSTEM WITH WIRELESS ARRAY FOR POWER AND DATA TRANSFER

SUMMARY

In accordance with the present disclosure, a surgical instrument comprises a shaft and an end effector extending from the shaft, the end effector comprising a staple cartridge comprising: a cartridge deck, a cartridge body, and a cartridge antenna supported by the cartridge body; a longitudinal channel, comprising: a base, a first wall extending from the base, a second wall extending from the base, wherein the second wall is spaced apart from the first wall to accommodate the staple cartridge therebetween in an assembled configuration, and a channel antenna supported by the first wall, wherein the cartridge antenna and the channel antenna are to cooperatively define a wireless signal-transfer circuit in the assembled configuration; and an aligner to interlock the staple cartridge and the longitudinal channel in the assembled configuration, wherein the aligner is adjacent the channel antenna and the staple cartridge antenna to maintain a predefined spatial relation between the channel antenna and the cartridge antenna in the assembled configuration.

DRAWINGS

In the description, for purposes of explanation and not limitation, specific details are set forth, such as particular procedures, techniques, etc. to provide a thorough understanding of the present technology. However, it will be apparent to one skilled in the art that the present technology may be practiced in other aspects that depart from these specific details.

The accompanying drawings, together with the detailed description below, are incorporated in and form part of the specification, and serve to further illustrate aspects of concepts that include the claimed disclosure and explain various principles and advantages of those aspects.

The apparatuses and methods disclosed herein have been represented where appropriate by conventional symbols in the drawings, showing only those specific details that are pertinent to understanding the various aspects of the present disclosure so as not to obscure the disclosure with details that will be readily apparent to those of ordinary skill in the art having the benefit of the description herein.

Corresponding reference characters indicate corresponding items throughout the several views.

DETAILED DESCRIPTION

Figure 1:
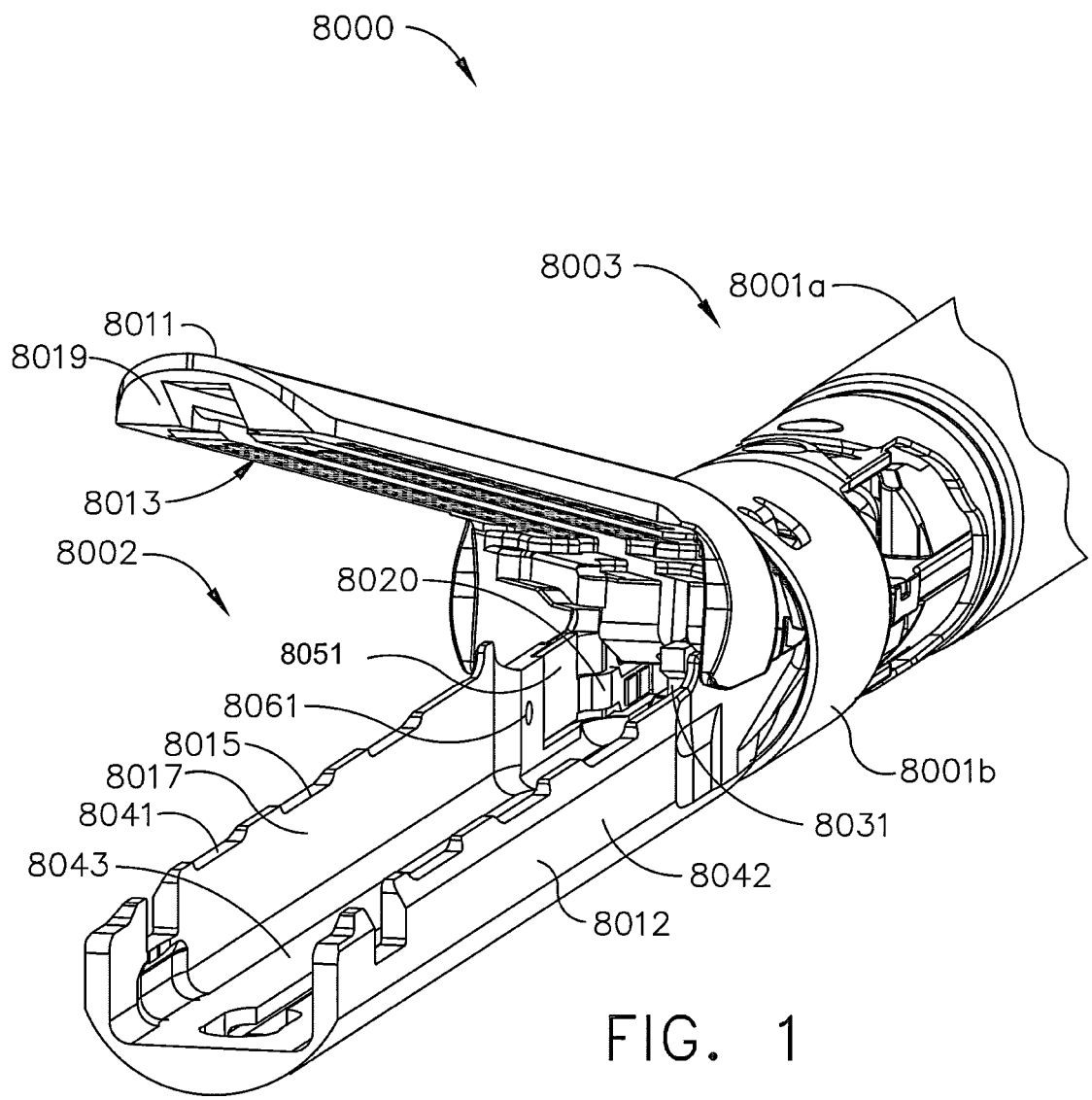
FIG. 1 is a partial perspective view of a surgical instrument including an end effector with a channel antenna for wireless transmission of power and/or data, in accordance with the present disclosure.

Applicant of the present application owns the following U.S. Patent Applications that were filed on Oct. 13, 2023 and which are each herein incorporated by reference in their respective entireties:

U.S. patent application Ser. No. 18/379,759, titled METHOD OF OPERATING A SURGICAL STAPLING INSTRUMENT, now U.S. Patent Application Publication No. 2025/0120695;

U.S. patent application Ser. No. 18/379,762, titled SURGICAL STAPLING SYSTEMS WITH ADAPTIVE STAPLE FIRING ALGORITHMS, now U.S. Patent Application Publication No. 2025/0120696;

U.S. patent application Ser. No. 18/379,763, titled LEARNED TRIGGERS FOR ADAPTIVE CONTROL OF SURGICAL STAPLING SYSTEMS, now U.S. Patent Application Publication No. 2025/0120711;

U.S. patent application Ser. No. 18/379,766, titled CONTROL CIRCUIT FOR ACTUATING MOTORIZED FUNCTION OF SURGICAL STAPLING INSTRUMENT UTILIZING INERTIAL DRIVE TRAIN PROPERTIES, now U.S. Patent Application Publication No. 2025/0120697;

U.S. patent application Ser. No. 18/379,768, titled PROPORTIONATE BALANCING OF THE FUNCTION IMPACT MAGNITUDE OF BATTERY OUTPUT TO PEAK MOTOR CURRENT, now U.S. Patent Application Publication No. 2025/0120692;

U.S. patent application Ser. No. 18/379,771, titled MOTOR OPTIMIZATION BY MINIMIZATION OF PARASITIC LOSSES AND TUNING MOTOR DRIVE CONFIGURATION, now U.S. Pat. No. 12,274,440;

U.S. patent application Ser. No. 18/379,773, titled APPARATUS AND METHOD TO REDUCE PARASITIC LOSSES OF THE ELECTRICAL SYSTEM OF A SURGICAL INSTRUMENT, now U.S. Patent Application Publication No. 2025/0120683;

U.S. patent application Ser. No. 18/379,776, titled SURGICAL TOOL WITH RELAXED FLEX CIRCUIT ARTICULATION, now U.S. Patent Application Publication No. 2025/0120732;

U.S. patent application Ser. No. 18/379,777, titled WIRING HARNESS FOR SMART STAPLER WITH MULTI AXIS ARTICULATION, now U.S. Patent Application Publication No. 2025/0120693; and U.S. patent application Ser. No. 18/379,784, titled SURGICAL STAPLE CARTRIDGE COMPRISING REPLACEABLE ELECTRONICS PACKAGE; now U.S. Pat. No. 12,193,670.

Applicant of the present application owns the following U.S. Patent Applications that were filed on Oct. 13, 2023 and which are each herein incorporated by reference in their respective entireties:

U.S. patent application Ser. No. 18/379,790, titled METHOD OF ASSEMBLING A STAPLE CARTRIDGE, now U.S. Patent Application Publication No. 2025/0120700;

U.S. patent application Ser. No. 18/379,793, titled CONTROL SURFACES ON A STAPLE DRIVER OF A SURGICAL STAPLE CARTRIDGE, now U.S. Patent Application Publication No. 2025/0120712;

U.S. patent application Ser. No. 18/379,796, titled INTEGRAL CARTRIDGE STIFFENING FEATURES TO REDUCE CARTRIDGE DEFLECTION, now U.S. Patent Application Publication No. 2025/0120701;

U.S. patent application Ser. No. 18/379,801, titled STAPLE CARTRIDGE COMPRISING WALL STRUCTURES TO REDUCE CARTRIDGE DEFLECTION, now U.S. Patent Application Publication No. 2025/0120702;

U.S. patent application Ser. No. 18/379,803, titled PANLESS STAPLE CARTRIDGE ASSEMBLY COMPRISING RETENTION FEATURES FOR HOLDING STAPLE DRIVERS AND SLED, now U.S. Patent Application Publication No. 2025/0120713;

U.S. patent application Ser. No. 18/379,805, titled STAPLE CARTRIDGE COMPRISING A SLED HAVING A DRIVER LIFT CAM, now U.S. Pat. No. 12,279,769;

U.S. patent application Ser. No. 18/379,808, titled SURGICAL STAPLE CARTRIDGES WITH SLEDS CONFIGURED TO BE COUPLED TO A FIRING DRIVER OF A COMPATIBLE SURGICAL STAPLER, now U.S. Patent Application Publication No. 2025/0120704;

U.S. patent application Ser. No. 18/379,810, titled STAPLE CARTRIDGE COMPRISING A COMPOSITE SLED, now U.S. Patent Application Publication No. 2025/0120705;

U.S. patent application Ser. No. 18/379,811, titled SURGICAL INSTRUMENTS WITH JAW AND FIRING ACTUATOR LOCKOUT ARRANGEMENTS LOCATED PROXIMAL TO A JAW PIVOT LOCATION, now U.S. Patent Application Publication No. 2025/0120706;

U.S. patent application Ser. No. 18/379,815, titled SURGICAL INSTRUMENTS WITH LATERALLY ENGAGEABLE LOCKING ARRANGEMENTS FOR LOCKING A FIRING ACTUATOR, now U.S. Patent Application Publication No. 2025/0120707;

U.S. patent application Ser. No. 18/379,817, titled DUAL INDEPENDENT KEYED LOCKING MEMBERS ACTING ON THE SAME DRIVE MEMBER, now U.S. Patent Application Publication No. 2025/0120714;

U.S. patent application Ser. No. 18/379,820, titled ADJUNCTS FOR USE WITH SURGICAL STAPLING INSTRUMENTS, now U.S. Pat. No. 12,295,578;

U.S. patent application Ser. No. 18/379,822, titled ADJUNCTS FOR USE WITH SURGICAL STAPLING INSTRUMENTS, now U.S. Patent Application Publication No. 2025/0120694;

U.S. patent application Ser. No. 18/379,826, titled JAW CONTROL SURFACES ON A SURGICAL INSTRUMENT JAW, now U.S. Patent Application Publication No. 2025/0120733;

U.S. patent application Ser. No. 18/379,827, titled ZONED ALGORITHM ADAPTIVE CHANGES BASED ON CORRELATION OF COOPERATIVE COMPRESSION CONTRIBUTIONS OF TISSUE, now U.S. Pat. No. 12,295,576;

U.S. patent application Ser. No. 18/379,831, titled STAPLE CARTRIDGES COMPRISING TRACE RETENTION FEATURES, now U.S. Patent Application Publication No. 2025/0120708; and U.S. patent application Ser. No. 18/379,832, titled STAPLE CARTRIDGES COMPRISING STAPLE RETENTION FEATURES, now now U.S. Patent Application Publication No. 2025/0120716;

Certain examples in accordance with the present disclosure will now be described to provide an overall understanding of the principles of the structure, function, manufacture, and use of the devices and methods disclosed herein. One or more examples of the present disclosure are illustrated in the accompanying drawings. The features illustrated or described in connection with the present disclosure may be combined with the various features in accordance with the present disclosure. Such modifications and variations are intended to be included within the scope of the present invention.

Reference throughout the specification to particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various methods, instruments, and systems are provided for performing surgical procedures. Various surgical systems disclosed herein include working portions that can be inserted into a body in any way, such as through a natural orifice, through an incision or puncture hole formed in tissue, etc. The working portions or end effector portions can be inserted directly into a patient's body or can be inserted through an access device that has a working channel. As the present Detailed Description proceeds, it will be understood that the various unique and novel arrangements of the various forms of surgical systems disclosed herein may be effectively employed in connection with robotically-controlled surgical systems and/or hand-held surgical systems. Various robotic systems, instruments, components and methods are disclosed in U.S. patent application Ser. No. 13/118,241, entitled SURGICAL STAPLING INSTRUMENTS WITH ROTATABLE STAPLE DEPLOYMENT ARRANGEMENTS, which is incorporated by reference herein in its entirety.

With an industry shift toward smart cartridges arises a need for an effective transmission of power and/or data between the surgical instrument and disposable smart cartridges. Chips, sensors, and/or other electrical components on the staple cartridges provide tremendous functionality, but require higher power and better communication capabilities. Physical electrical interfaces between the surgical instrument and the staple cartridge are capable of meeting the power/data requirements, but suffer from exposure to saline and/or other bodily fluids during a surgical procedure, which can negatively impact power and/or data transmission.

Power and/or data transmission between the surgical instrument and the staple cartridge can also be accomplished wirelessly using wireless antennas, as described in greater detail below. Nonetheless, size constraints (e.g., diameter of antenna coil is roughly equivalent to the maximum transmission distance) can be quite taxing on the antenna coils' ability to meet the higher power and/or data transmission requirements. Moreover, slight misalignments between the antenna coils can seriously impact the ability of the antenna coils to effectively transmit power and/or data wirelessly therebetween. The present disclosure can provide technical solutions for ensuring effective power and/or data transmission between a surgical instrument (e.g., surgical instrument 8000) and a disposable cartridge (e.g., staple cartridge 8040).

FIG. 1 is a partial perspective view of a surgical instrument 8000, in accordance with the present disclosure. The surgical instrument 8000 includes a shaft 8001 that defines a central longitudinal axis 8005 extending therethrough. The shaft 8001 includes a proximal shaft portion 8001a that can be coupled to a handle if the surgical instrument is handheld. Alternatively, the proximal shaft portion 8001a may include a housing for coupling to a robotic arm of a surgical robot, for example.

The shaft 8001 further includes a distal shaft portion 8001b coupled to an end effector 8002. An articulation joint assembly 8003 extends between the proximal shaft portion 8001a and the distal shaft portion 8001b. The articulation joint assembly 8003 includes an articulation driver movable distally to rotate the end effector 8002 from an unarticulated position toward an articulated position. The articulation joint assembly 8003 can be removed, and the proximal shaft portion 8001a and the distal shaft portion 8001b define a continuous shaft.

Figure 2:
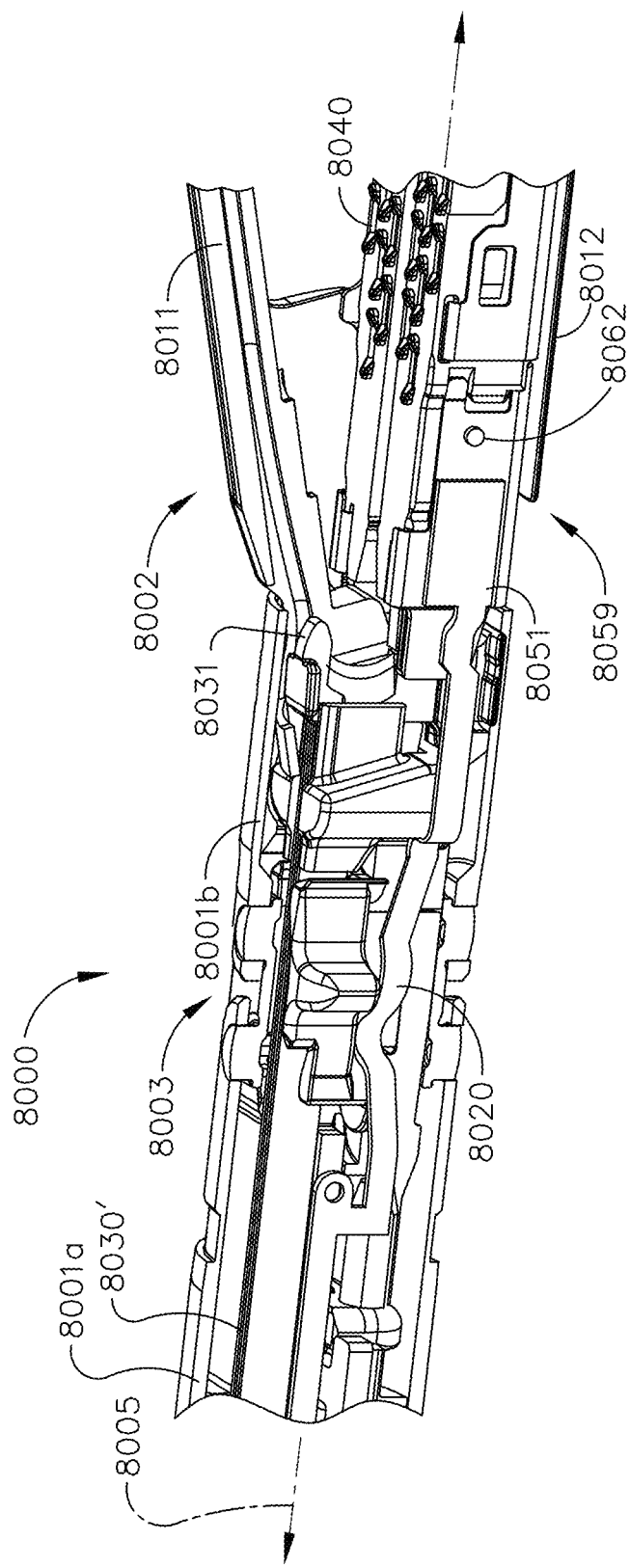
FIG. 2 is a partial cross-sectional view of the surgical instrument of FIG. 1 in an assembled configuration with a staple cartridge including a cartridge antenna, in accordance with the present disclosure.

Further to the above, the end effector 8002 includes a first jaw 8011 and a second jaw 8012 movable relative to the first jaw 8011 to transition the end effector 8002 from an open configuration, as illustrated in FIG. 1, to a closed configuration to grasp tissue, for example, between the first jaw 8011 and the second jaw 8012. In the illustrated example, the first jaw 8011 comprises an anvil 8019 including staple forming pockets 8013 and the second jaw 8012 includes a longitudinal channel 8015 designed and sized to receive a staple cartridge 8040, as illustrated in FIG. 2. The staple cartridge 8040 is removably insertable in the longitudinal channel 8015. The staple cartridge 8040 and the longitudinal channel 8015 can be transitioned between an assembled configuration, wherein the staple cartridge 8040 is positioned in the longitudinal channel 8015, and an unassembled configuration where the staple cartridge 8040 is separate from the longitudinal channel 8015. The staple cartridge 8040 includes staples deformable against the staple forming pockets 8013 of the anvil 8019, in the assembled configuration. As described in greater detail below, the staple cartridge 8040 is configured for wireless transmission of power and/or data with the surgical instrument 8000, in an assembled configuration, as illustrated in FIG. 1.

While the present disclosure can be explained in the context of a linear stapler, this should not be construed as limiting. The present disclosure can readily be implemented in other types of surgical instruments that employ smart cartridges.

In the illustrated example, a drive shaft 8030 extends distally along the longitudinal central axis 8005. The drive shaft 8030 is coupled to a firing beam 8031, and is movable by the drive shaft 8030 to motivate a sequential deployment of staples from the staple cartridge 8040, and motivate a cutting of the stapled tissue by a knife on the firing beam 8031, for example. Additional details are described in U.S. patent application Ser. No. 14/200,111, entitled CONTROL SYSTEMS FOR SURGICAL INSTRUMENTS, filed Mar. 7, 2014, which issued on Apr. 25, 2017 as U.S. Pat. No. 9,629,629, which is hereby incorporated by reference herein in its entirety.

The closure of the end effector 8002 can be driven separately, e.g., by a closure tube, from staple firing. A closure tube could motivate one, or both, the jaws 8011, 8012 to move toward the closed configuration prior to, or concurrently with, advancement of the firing beam 8031 to deploy the stapes and cut the tissue grasped by the end effector 8002.

The surgical instrument 8000 further includes a wiring harness 8020 comprising a flex circuit that transmits at least one of data or power through the articulation joint assembly 8003 to the end effector 8002 from a power source or a data source proximal to the articulation joint assembly 8003. The flex circuit can transmit power to the end effector 8002 for powering an electronics package that communicates with a chip in the staple cartridge 8040, for example. A wireless signal-transfer circuit 8050 (FIG. 4) facilitates a wireless transmission of power and/or data between the flex circuit 8020 and the chip of the staple cartridge 8040, as described below in greater detail. Additionally, the flex circuit may define a communication pathway between the chip and a processor and/or a power source of the surgical instrument 8000 positioned proximal to the articulation joint assembly 8003.

The flex circuit can comprise floating ends. The flex circuit can comprise fixed ends. The flex circuit can comprise one floating end and one fixed end. The flex circuit can include a flexible substrate and a conductive layer disposed on the flexible substrate.

The interconnecting wiring harness 8020 can be comprise of twisted wire pairs or a flex circuit with similar shielding or overlapping conductors, for example, in order to minimize the electrical coupling to adjacent metallic components that may cause parasitic losses. The flex circuit may include a shielding layer that can be integrated into some of the layers of the flex circuit, for example, for magnetic coupling mitigation. The flex circuit traces can be overlaid in a twisted pair pattern to minimize the magnetic coupling to external metal and, thereby, minimize the creation of reinforced magnetic fields, for example. The flex circuit can be coiled/twisted down the entirety of the pathway of the wiring harness 8020, which can be the entire, or at least part of the entire, length of the shaft 8001, for example.

The coiled flex circuit allows for longitudinal movement of the flexible circuit. The flex circuit can be put into the twist-curl shape, which allows the flex circuit to have some shape memory. Accordingly, the coiled flex circuit may extend, then retract to an original shape, with articulation of the end effector 8001, for example, without risking damage to flex circuit components.

Figure 4:
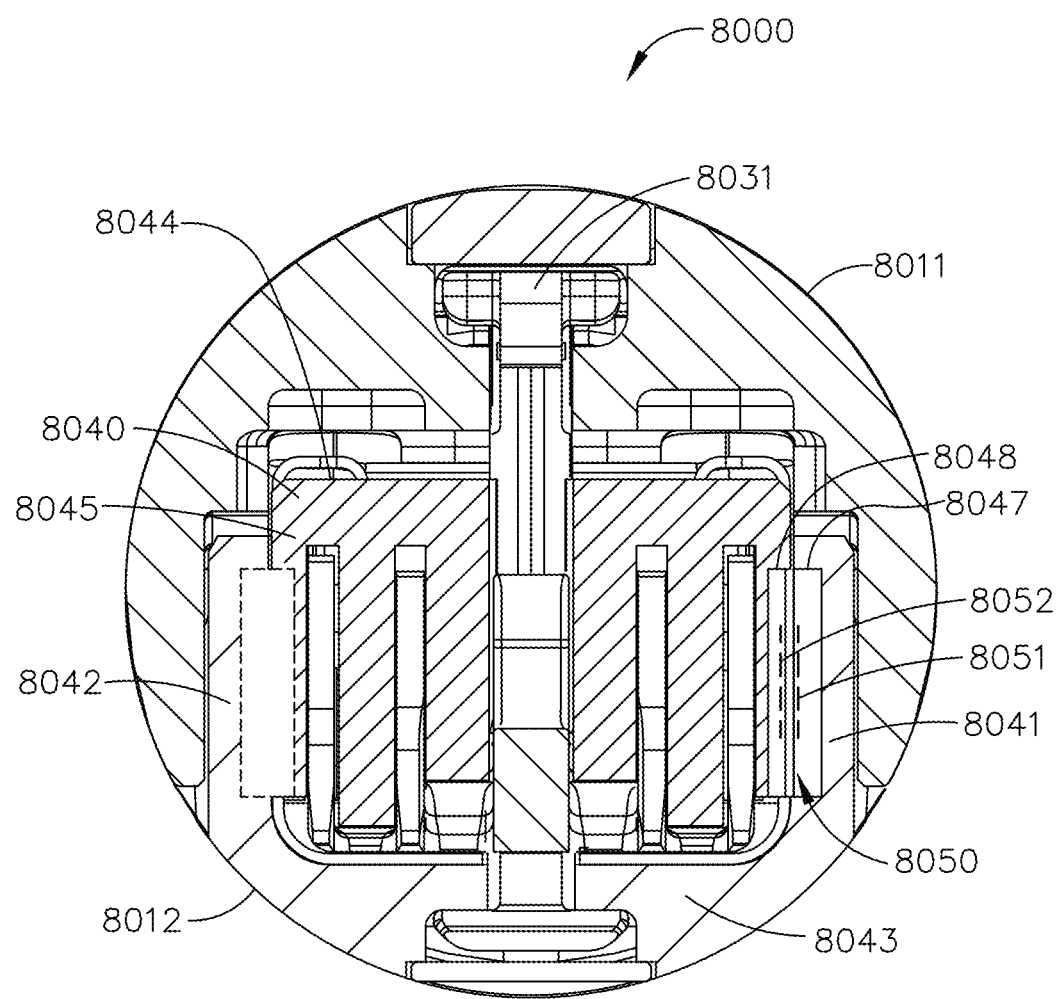
FIG. 4 is a cross-sectional view of the end effector of FIG. 2, in accordance with the present disclosure.

As best illustrated in FIG. 4, the wireless signal-transfer circuit 8050 includes a channel antenna 8051 and a cartridge antenna 8052. Moreover, the surgical instrument 8000 further includes an aligner 8060 that interlocks the staple cartridge 8040 and the longitudinal channel 8015 in the assembled configuration. The aligner 8060 is adjacent the channel antenna 8051 and the cartridge antenna 8051 in the assembled configuration to maintain a predefined spatial relation between the channel antenna 8051 and the cartridge antenna 8052.

Figure 3:
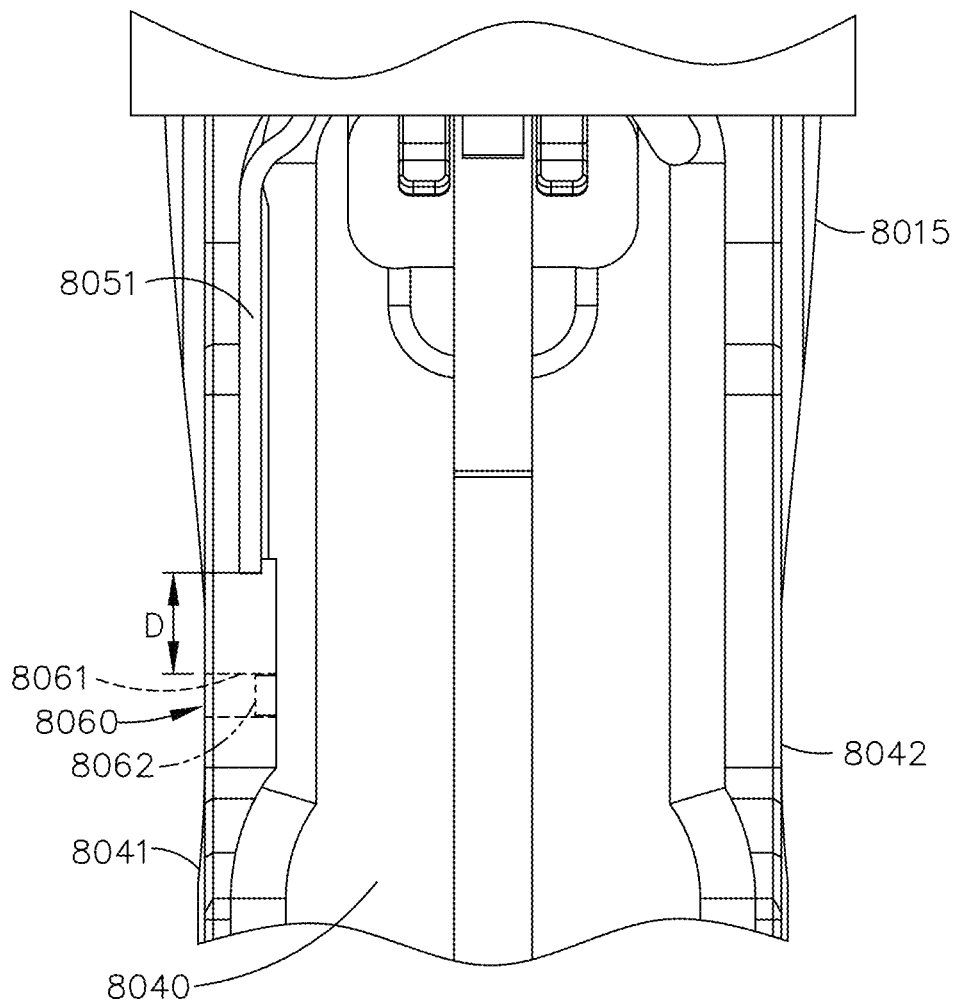
FIG. 3 is a partial cross-sectional view of the surgical instrument of FIG. 1, in accordance with the present disclosure.

Referring to FIGS. 1, 3, and 4, the longitudinal channel 8015 includes a base 8043, a first wall 8041 and a second wall 8042 extending from the base 8043. The second wall 8042 is spaced apart from the first wall 8041 to accommodate the staple cartridge 8040 therebetween in the assembled configuration. The channel antenna 8051 is housed in a cavity of the first wall 8041. A second channel antenna can be housed in a cavity of the second wall 8042. The channel antenna 8051 can be attached to, and protrudes from, the first wall 8041.

Referring primarily to FIGS. 3 and 4, the staple cartridge 8040 includes a cartridge deck 8044 that includes staple cavities, and a cartridge body 8045 housing staples driven through the staple cavities for deployment into tissue grasped between the staple cartridge 8040 and the staple forming pockets 8013 of the anvil 8019. As illustrated, the cartridge body 8045 can support the cartridge antenna 8052 for positioning against the channel antenna 8051 in the assembled configuration. As best illustrated in FIG. 4, the cartridge antenna 8052 is housed in a cavity in the cartridge body 8045. The cartridge antenna 8052 can be attached to, and protrudes from, the cartridge body 8045.

The aligner 8060 includes a channel alignment component 8061 (FIG. 1) defined in longitudinal channel 8015 and a corresponding cartridge alignment component 8062 (FIG. 2) of the staple cartridge 8040, which cooperates with the channel alignment component 8061 in the assembled configuration to maintain the channel antenna 8051 and the cartridge antenna 8052 in a predefined spatial relation. The aligner 8060 can define an interlocking, or mating, interface between the channel alignment component 8061 and the cartridge alignment component 8062, to maintain the predetermined spatial relation between the antennas 8051, 8052.

As illustrated in FIGS. 3 and 4, the channel alignment component 8061 can be in the form of a cavity, slot, or opening, and the cartridge alignment component 8062 can be in the form of a projection, post, or guide to be received in the channel alignment component 8061 in the assembled configuration. Alternatively, the cartridge alignment component 8062 can be in the form of a cavity, slot, or opening, and the channel alignment component 8061 can be in the form of a projection, post, or guide to be received in the channel alignment component 8061 in the assembled configuration. Other alignment components are contemplated by the present disclosure.

The predetermined spatial relation between the antennas 8051, 8052, as defined by the interlocking interface of the components of the aligner 8060, comprises a translational misalignment tolerance of less than or equal to a predefined distance. The translational misalignment tolerance includes a tolerance in one or more dimensions such as, for example, a longitudinal translational misalignment tolerance, a transverse translational misalignment tolerance, and/or a vertical translational misalignment tolerance. The aligner 8060 is to resist longitudinal, vertical, and/or transverse movement, or sliding, of the staple cartridge 8040 relative to the longitudinal channel 8015 in the assembled configuration, to ensure a proper alignment of the antennas 8051, 8052.

Additionally, or alternatively, the predetermined spatial relation comprises an angular misalignment tolerance of less than or equal to a predefined angle. The interlocking interface of the components of the aligner 8060 resists pitch, yaw, and/or roll movement of the staple cartridge 9040 relative to the longitudinal channel 8015.

The translational misalignment tolerance and/or the angular misalignment tolerance can be selected from a range of about 0.01% to about 10%, for example. Other values and/or ranges are contemplated by the present disclosure. The aligner 8060 can ensure a translational misalignment less than or equal to +5 mm, +3 mm, or +1 mm, for example. The aligner 8060 can ensure an angular misalignment of less than or equal to +5°, +3°, or +1°, for example.

The aligner 8060 can maintain an air-gap distance between the antennas 8051, 8052, in the assembled configuration, of about 4.5 mm. In some aspects, the air-gap distance is any value selected from a range of about 3 mm to about 10 mm, for example.

The alignment components 8061, 8062 can be designed in an offset configuration to resolve a manufacturing-induced misalignment between the channel antenna 8051 and the cartridge antenna 8052 in the assembled configuration. The manufacturing-induced misalignment may be due cartridge shrinkage. The designed offset between the alignment components 8061, 8062 can be tuned to address the manufacturing-induced misalignment.

An important characteristic of the aligner 8060 is its distance from the antennas 8051, 8052 in the assembled configuration. To effectively maintain the predetermined spatial relation between the antennas 8051, 8052, in a manner that ensures efficient/optimal power and/or data transfer therebetween, the aligner 8060 is to be positioned a predetermined distance (D), FIG. 4, from the antennas 8051, 8052. The distance (D) is selected from a range of about 1 mm to about 60 mm. The distance (D) can be selected from a range of about 5 mm to about 30 mm, or about 10 mm to about 20 mm. The distance (D) can be about 15 mm, for example.

The aligner 8060 and the antennas 8051, 8052 are located at a proximal portion 8059 of the end effector 8002, as best illustrated in FIG. 2. Alternatively, the aligner 8060 and the antennas 8051, 8052 can be located at an intermediate portion, or a distal portion, of the end effector 8002. Nonetheless, the position of the aligner 8060 and the antennas 8051, 8052 at the proximal portion reduces the length of the wiring harness 8020 needed to transmit power and/or data to/from the channel antenna 8051, which reduces parasitic losses and/or signal interference.

The aligner 8060 is positioned distal to the antennas 8051, 8052 in the assembled configuration, as illustrated in FIG. 2. Nonetheless, in other configurations, the aligner 8060 can be positioned proximal to the antennas 8051, 8052 in the assembled configuration. In yet other configurations, more than one aligner 8060 can be utilized. For example, in some configurations, an aligner 8060 can be positioned distal to the antennas 8051, 8052, and another aligner can be positioned proximal to the antennas 8051, 8052, such that the antennas 8051, 8052 are positioned between two aligners, in the assembled configuration, for example.

Figure 5:
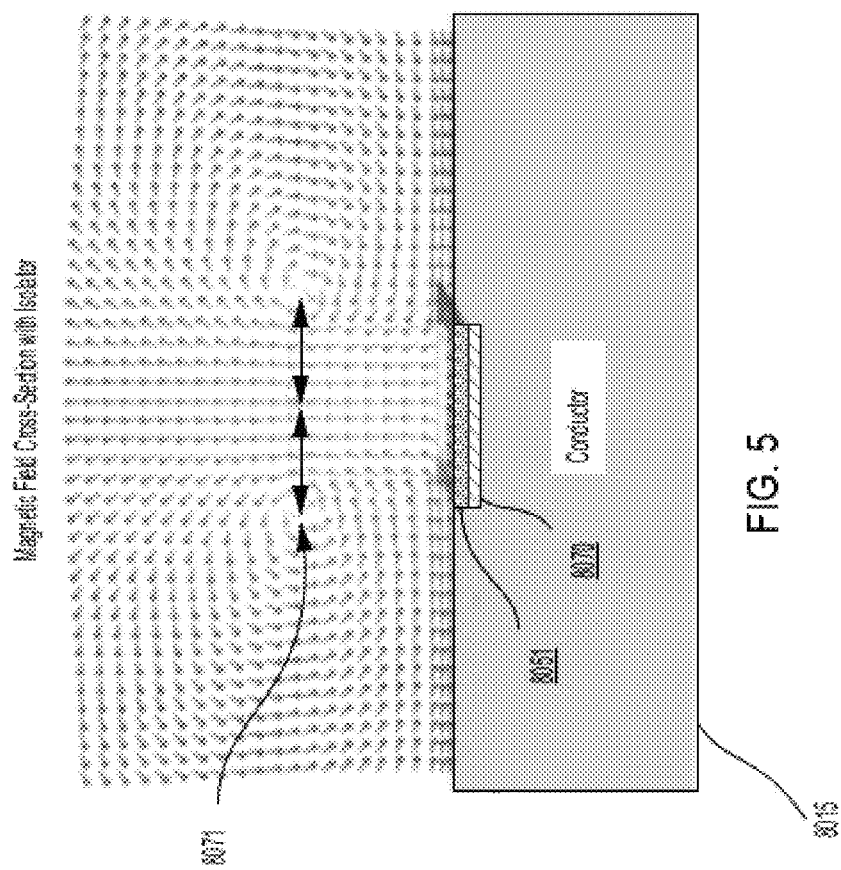
FIG. 5 is a partial cross-sectional view of a longitudinal channel including an antenna and an insulative layer, in accordance with the present disclosure.

Referring primarily to FIG. 5, one or both of the antennas 8051, 8052 can be disposed onto an intermediate insulative, or non-conductive, layer 8070 to improve efficiency of power and/or data transfer between the antennas 8051, 8052, by reducing parasitic to neighboring surfaces such as, for example, to the longitudinal channel 8015. In the insulative, or non-conductive, layer 8070 focuses a magnetic field pattern 8071 between the antennas 8051, 8052, thereby preventing, or reducing, magnetic field drainage directed in its direction and/or wrapping fields directed in other directions, as illustrated in FIG. 5. The insulative, or non-conductive, layer 8070 may comprise a Urethane foam. The insulative, or non-conductive, layer 8070 may comprise silicone EMI. The insulative, or non-conductive, layer 8070 may comprise a microwave shielding material impregnated with carbon fibers or magnetically loaded, for example. The insulative, or non-conductive, layer 8070 may comprise ECCOSORF™.

Figure 6:
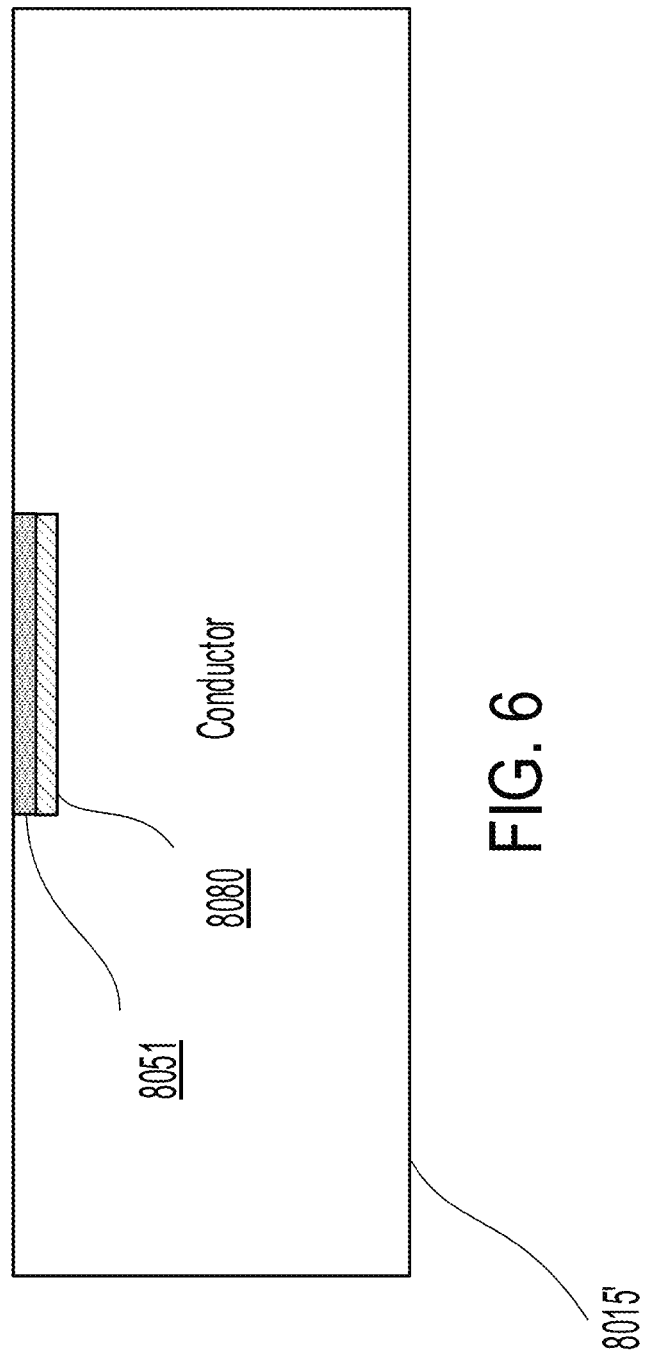
FIG. 6 is partial cross-sectional view of a longitudinal channel including an antenna and a ferrite layer, in accordance with the present disclosure.

Instead of the insulative, or non-conductive, layer 8070, or in addition thereto, a ferrite shield 8080 can be utilized to focus/manage the magnetic field in the inductive coupling between the antennas 8051, 8052. FIG. 6 illustrates a longitudinal channel 8015', similar in many respects to the longitudinal channel 8015, wherein a ferrite shield 8080 is disposed between the longitudinal channel 8015' and the channel antenna 8051. Additionally, or alternatively, a similar ferrite shield can be disposed between the cartridge body 8045 and the cartridge antenna 8052, for example. Additionally, or alternatively, a ferrite shield can be disposed between the antennas 8051, 8052, for example.

Figure 7:
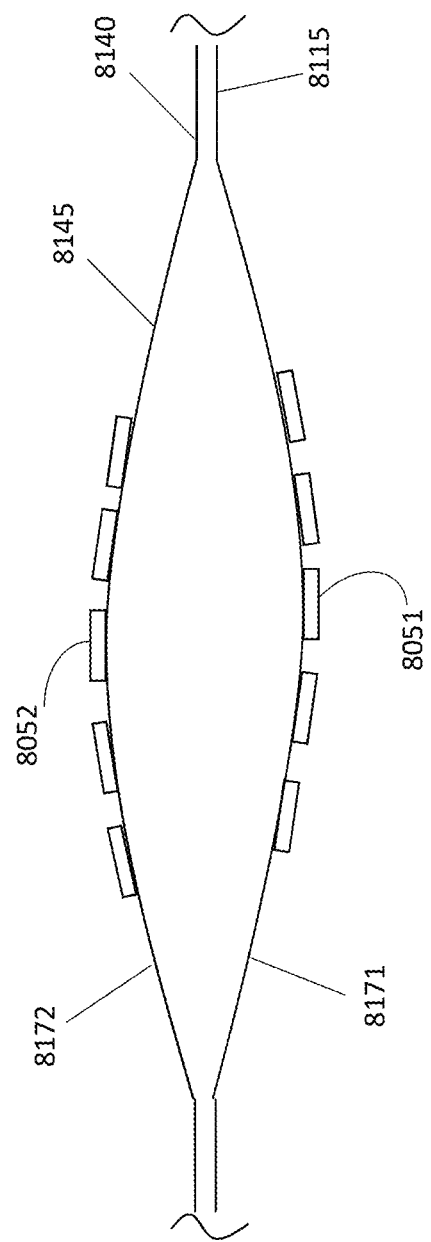
FIG. 7 is partial cross-sectional view of a longitudinal channel and a staple cartridge in an assembled configuration, in accordance with the present disclosure.

FIG. 7 illustrates alternative longitudinal channel 8115 and staple cartridge 8140 in an assembled configuration. The longitudinal channel 8115 and staple cartridge 8140 are similar in many respects to the longitudinal channel 8015 and staple cartridge 8040, which are not repeated herein for brevity. Alternatively, the surgical instrument 8000 may include the longitudinal channel 8115 instead of the longitudinal channel 8015. The staple cartridge 8140 can be removably received in the longitudinal channel 8115, in the assembled configuration.

The longitudinal channel 8115 and staple cartridge 8140 comprise cavities 8171, 8172, respectively, defined in corresponding outer surfaces thereof, as illustrated in FIG. 7. The cavities 8171, 81712 define curved, or concave, zones, or surfaces, that accommodate the antennas 8051, 8052, respectively. The arcuate disposition of the antennas 8051, 8052 along the curved zones of the cavities 8171, 8172 provides a three-dimensional effect that focuses the transmission field between the antennas 8051, 8052. Alternatively, only the longitudinal channel 8115 or staple cartridge 8140 may comprise a curved antenna disposition, while the other remains flat, or at least substantially flat.

Figure 8:
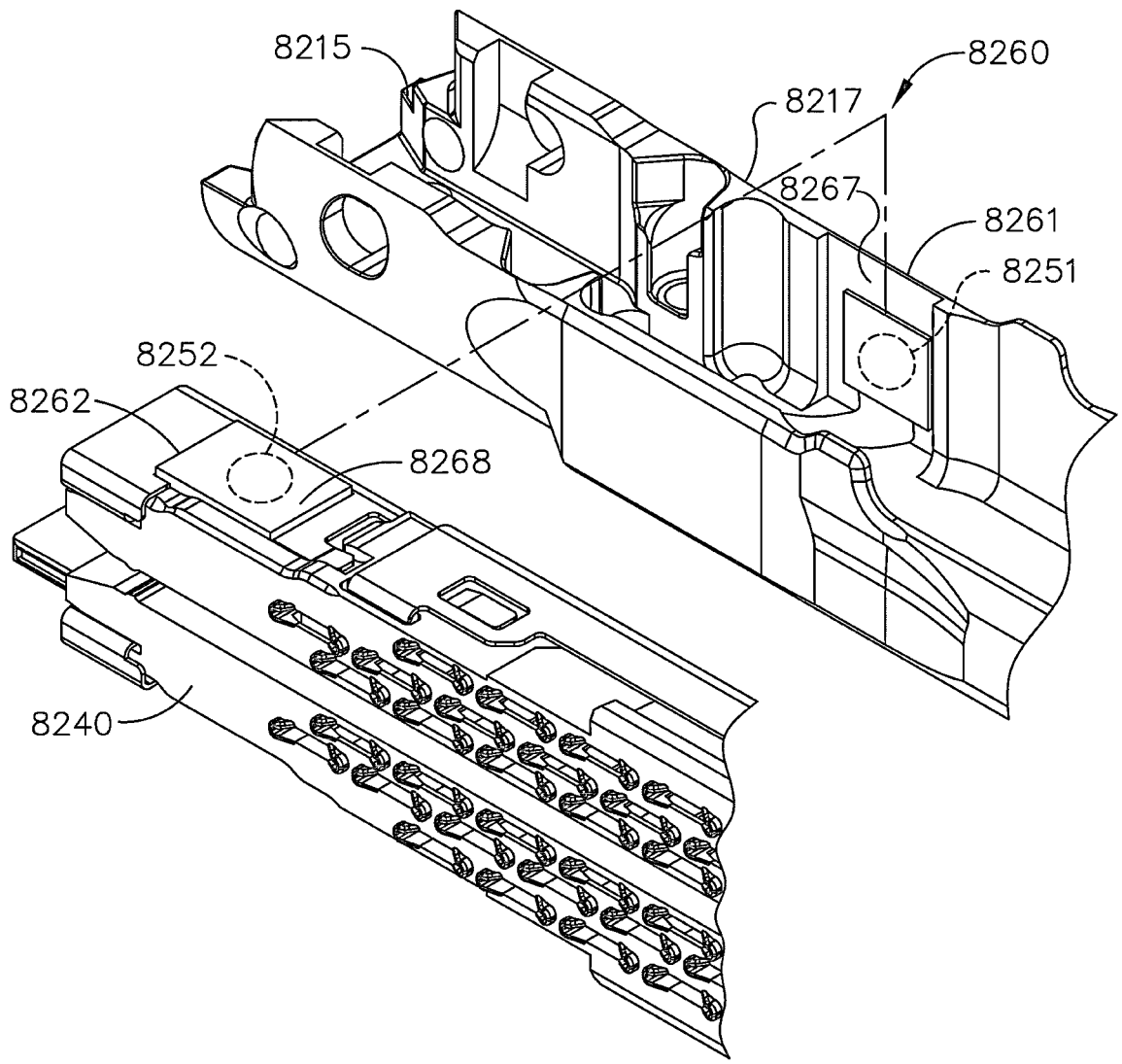
FIG. 8 is a partial perspective view of a staple cartridge and a longitudinal channel, in accordance with the present disclosure.

FIG. 8 illustrates alternative longitudinal channel 8215 and staple cartridge 8240 that are similar in many respects to the longitudinal channel 8015 and staple cartridge 8040, which are not repeated herein for brevity. Alternatively, the surgical instrument 8000 may include the longitudinal channel 8215 instead of the longitudinal channel 8015. The staple cartridge 8240 can be removably received in the longitudinal channel 8215, in the assembled configuration.

The longitudinal channel 8215 and staple cartridge 8240 cooperatively form an aligner 8260 that incorporates, or integrates, antennas 8251, 8252 into a channel alignment component 8261 and cartridge alignment component 8262, respectively. As illustrated in FIG. 8, the antennas 8251, 8252 can be positioned on, or embedded in, the channel alignment component 8261 and cartridge alignment component 8262, respectively.

The staple cartridge 8240 is similar in many respects to the staple cartridge 8040, which are not repeated herein for brevity. The cartridge alignment component 8262 is positioned on a cartridge body 8245 of the staple cartridge 8240, and is shaped and sized for a matting engagement with the channel alignment component 8261 defined on a side wall 8217 of the longitudinal channel 8215.

The channel alignment component 8261 includes a depression, or cavity 8267, defined in the side wall 8217. The cartridge alignment component 8262 includes a corresponding projection 8268 for matting engagement with the cavity 8267. The antennas 8251, 8252 reside in the cavity 8267 and projection 8268, respectively. The antennas 8251, 8252 are within sufficiently close proximity for signal transmission therebetween when the projection 8268 is assembled with the cavity 8267.

Figure 9:
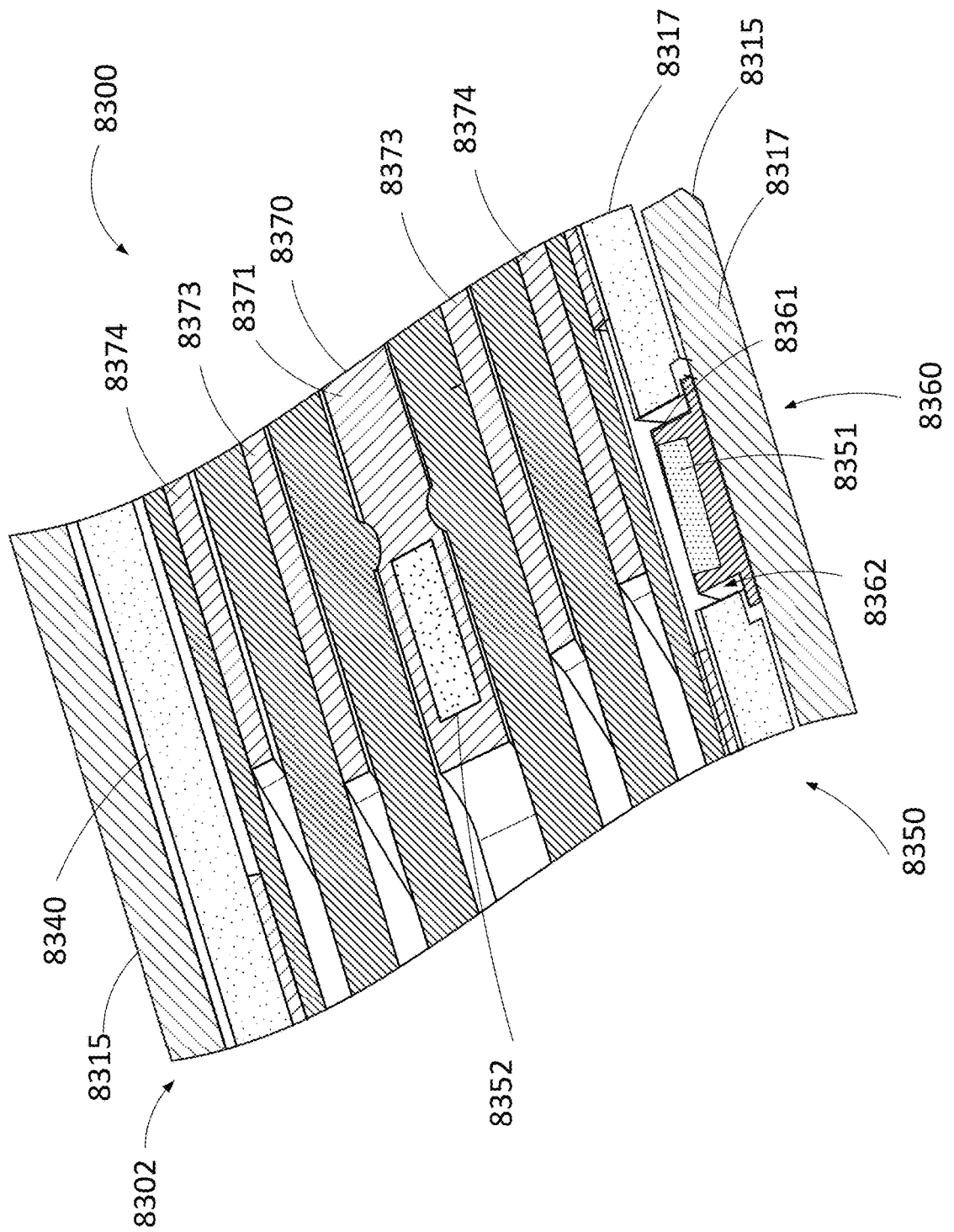
FIG. 9 is a partial cross-sectional view of a surgical instrument including a staple cartridge assembled with a longitudinal channel, in accordance with the present disclosure.

FIG. 9 is a partial cross-sectional view of a surgical instrument 8300 similar in many respects to the surgical instrument 8000, which are not repeated herein for brevity. For example, the surgical instrument 8300 includes a shaft 8001, and may include an articulation joint assembly 8003. The surgical instrument 8300 also includes an end effector 8302 with jaws for grasping tissue therebetween. Moreover, the end effector 8302 includes a longitudinal channel 8315 shaped and sized to retain a staple cartridge 8340.

The staple cartridge 8340 is removably insertable in the longitudinal channel 8315. The staple cartridge 8340 and the longitudinal channel 8315 can be transitioned between an assembled configuration, wherein the staple cartridge 8340 is positioned in the longitudinal channel 8315, and an unassembled configuration where the staple cartridge 8340 is separate from the longitudinal channel 8315. The staple cartridge 8340 includes staples deformable against staple forming pockets of an anvil of the end effector 8302, in the assembled configuration.

The staple cartridge 8340 is configured for wireless transmission of power and/or data with the surgical instrument 8300, in the assembled configuration, as illustrated in FIG. 9. The surgical instrument 8300 includes a wireless signal-transfer circuit 8350 similar in many respects to the wireless signal-transfer circuit 8050, which are not repeated herein for brevity. The wireless signal-transfer circuit 8350 is to transfer data and/or power between the surgical instrument 8300 and the staple cartridge 8340. While the wireless signal-transfer circuit 8050 includes cartridge antenna 8052 defined in the cartridge body of the staple cartridge 8015, the wireless signal-transfer circuit 8350 includes a cartridge antenna 8352 defined in, or housed in, a sled 8370 within the staple cartridge 8340.

The sled 8370 is movable distally from a home position (FIG. 9) during a firing motion to engage and lift staple drivers to eject staples from the staple cartridge 8340 into tissue grasped by the end effector 8302. The sled 8370 is a four-rail sled having a central upright 8371 configured to accommodate the cartridge antenna 8352, a pair of inner rails 8373, and a pair of outer rails 8374. The rails 8373, 8374 are to engage and lift the staple drivers during the firing motion to eject the staples from the staple cartridge 8340. The cartridge antenna 8352 can be housed in one of the rails 8373, 8374, for example.

The surgical instrument 8300 further includes a channel antenna 8351 positioned at a side wall of 8317 of the longitudinal channel 8315, in alignment with the cartridge antenna 8352, while the sled 8370 is in the home position, as illustrated in FIG. 9. An aligner 8360 interlocks the staple cartridge 8340 and the longitudinal channel 8315 in the assembled configuration to ensure a proper alignment between the antennas 8351, 8352 in the home position, for efficient transmission of power and/or data through the wireless signal-transfer circuit 8350.

The aligner 8360 is at a proximal portion of the end effector 8302, and is adjacent the channel antenna 8351 and the cartridge antenna 8352 in the assembled configuration. The aligner 8360 is configured to maintain a predefined spatial relation between the channel antenna 8351 and the cartridge antenna 8352, while the sled 8370 is in the home position.

The aligner 8360 includes a channel alignment component 8361 and a cartridge alignment component 8362 configured for matting engagement with the channel alignment component 8361. The alignment components 8361, 8362 are similar to the alignment components 8261, 8262, respectively. The channel alignment component 8361 protrudes, or outwardly extends, from the side wall 8317, and is configured to house the channel antenna 8351 therein. The cartridge alignment component 8362 defines an opening configured to receive the channel alignment component 8361 in the assembled configuration. Alternatively, the opening can be defined by the side wall 8317, and the protrusion by the cartridge body of the staple cartridge 8315. In any event, the channel alignment component 8361 and corresponding cartridge alignment component 8362, cooperatively maintain the channel antenna 8351 and the cartridge antenna 8352 in a predefined spatial relation.

Examples of the apparatus and method in accordance with the present disclosure are provided below in the following numbered clauses. The apparatus and method may include any one or more than one, and any combination of, the numbered clauses described below.

Example 1—A surgical instrument (8000) comprising a shaft (8001) and an end effector (8002) extending from the shaft, the end effector comprising a staple cartridge (8040) comprising: a cartridge deck (8044), a cartridge body (8045), and a cartridge antenna (8052) supported by the cartridge body; a longitudinal channel (8015), comprising: a base (8040), a first wall (8041) extending from the base, a second wall (8042) extending from the base, wherein the second wall is spaced apart from the first wall to accommodate the staple cartridge therebetween in an assembled configuration, and a channel antenna (8051) supported by the first wall, wherein the cartridge antenna and the channel antenna are to cooperatively define a wireless signal-transfer circuit (8050) in the assembled configuration; and an aligner (8060) to interlock the staple cartridge and the longitudinal channel in the assembled configuration, wherein the aligner is adjacent the channel antenna and the staple cartridge antenna to maintain a predefined spatial relation between the channel antenna and the cartridge antenna in the assembled configuration.

Example 2—The surgical instrument of Example 1, wherein maintaining the predefined spatial relation comprises a translational misalignment tolerance of less than or equal to a predefined distance, and an angular misalignment tolerance of less than or equal to a predefined angle.

Example 3—The surgical instrument of any of Examples 1-2, wherein the aligner resists a longitudinal sliding of the staple cartridge relative to the longitudinal channel in the assembled configuration.

Example 4—The surgical instrument of any of Examples 1-3, wherein the aligner resists a vertical sliding of the staple cartridge relative to the longitudinal channel in the assembled configuration.

Example 5—The surgical instrument of any of Examples 1-2, wherein the aligner is positioned at or below a maximum predefined distance from the wireless assembly in the assembled configuration.

Example 6—The surgical instrument of Example 5, wherein the maximum predefined distance is selected from a range of about 1 mm to about 60 mm.

Example 7—The surgical instrument of Example 5, wherein the maximum predefined distance is selected from a range of about 10 mm to about 20 mm.

Example 8—The surgical instrument of any of Examples 1-7, further comprising an articulation joint assembly (8003) extending between the shaft and the end effector, and a wiring harness (8020) to transmit at least one of data or power through the articulation joint, wherein the at least one of data or power is to be wirelessly transmitted between the cartridge antenna and the channel antenna in the assembled configuration.

Example 9—The surgical instrument of any of Examples 1-8, further comprising a ferrite layer (8080) deposed between the cartridge body and the cartridge antenna.

Example 10—The surgical instrument of Example 9, wherein the wiring harness comprises a twisted wire trace pattern.

Example 11—The surgical instrument of any of Examples 1-10, wherein the aligner comprises a first interlocking component at least partially extending around the channel antenna, and a second interlocking component at least partially extending around the cartridge antenna, wherein the second interlocking component and the first interlocking component cooperatively maintain the predefined spatial relation between the channel antenna and the cartridge antenna in the assembled configuration.

Example 12—The surgical instrument of Example 11, wherein the first interlocking component comprises a slot, and the second interlocking component comprises a tab to be received in the slot in the assembled configuration.

Example 13—The surgical instrument of any of Examples 1-12, wherein the cartridge body comprises a cartridge cavity (8267), and wherein the cartridge antenna is positioned in the cartridge cavity.

Example 14—The surgical instrument of Example 13, wherein the longitudinal channel comprises a channel cavity (8267), and wherein the channel antenna is positioned inside the channel cavity.

Example 15—The surgical instrument of Example 14, wherein the channel cavity and the cartridge cavity are shaped to cooperatively focus a wireless transmission between the cartridge antenna and the channel antenna in the assembled configuration.

Example 16—The surgical instrument of any of Examples 1-15, further comprising an insulative layer (8070) deposed between the longitudinal channel and the channel antenna.

Example 17—A surgical instrument comprising a shaft and an end effector extending from the shaft, the end effector comprising a staple cartridge comprising: a cartridge deck, a cartridge body, and a cartridge antenna supported by the cartridge body; a longitudinal channel, comprising: a base, a first wall extending from the base, a second wall extending from the base, wherein the second wall is spaced apart from the first wall to accommodate the staple cartridge therebetween in an assembled configuration, and a channel antenna supported by the first wall, wherein the cartridge antenna and the channel antenna are to cooperatively define a wireless signal-transfer circuit in the assembled configuration; and an aligner to interlock the staple cartridge and the longitudinal channel in the assembled configuration, wherein the aligner is adjacent the channel antenna and the staple cartridge antenna to maintain a predefined spatial relation between the channel antenna and the cartridge antenna in the assembled configuration.

Example 18—The surgical instrument of Example 17, wherein maintaining the predefined spatial relation comprises a translational misalignment tolerance of less than or equal to a predefined distance, and an angular misalignment tolerance of less than or equal to a predefined angle.

Example 19—The surgical instrument of Example 18, wherein the aligner resists a longitudinal sliding of the staple cartridge relative to the longitudinal channel in the assembled configuration.

Example 20—The surgical instrument of Examples 18, wherein the aligner resists a vertical sliding of the staple cartridge relative to the longitudinal channel in the assembled configuration.

Example 21—The surgical instrument of Example 18, wherein the aligner is positioned at or below a maximum predefined distance from the wireless assembly in the assembled configuration.

Example 22—The surgical instrument of Example 21, wherein the maximum predefined distance is selected from a range of about 1 mm to about 60 mm.

Example 23—The surgical instrument of Example 21, wherein the maximum predefined distance is selected from a range of about 10 mm to about 20 mm.

Example 24—The surgical instrument of Example 17, further comprising an articulation joint assembly extending between the shaft and the end effector, and a wiring harness to transmit at least one of data or power through the articulation joint, wherein the at least one of data or power is to be wirelessly transmitted between the cartridge antenna and the channel antenna in the assembled configuration.

Example 25—The surgical instrument of Example 24, further comprising a ferrite layer deposed between the cartridge body and the cartridge antenna.

Example 26—The surgical instrument of Example 25, wherein the wiring harness comprises a twisted wire trace pattern.

Example 27—The surgical instrument of Example 18, wherein the aligner comprises a first interlocking component at least partially extending around the channel antenna, and a second interlocking component at least partially extending around the cartridge antenna, wherein the second interlocking component and the first interlocking component cooperatively maintain the predefined spatial relation between the channel antenna and the cartridge antenna in the assembled configuration.

Example 28—The surgical instrument of Example 27, wherein the first interlocking component comprises a slot, and the second interlocking component comprises a tab to be received in the slot in the assembled configuration.

Example 29—The surgical instrument of Example 17, wherein the cartridge body comprises a cartridge cavity, and wherein the cartridge antenna is positioned in the cartridge cavity.

Example 30—The surgical instrument of Example 29, wherein the longitudinal channel comprises a channel cavity, and wherein the channel antenna is positioned inside the channel cavity.

Example 31—The surgical instrument of Example 30, wherein the channel cavity and the cartridge cavity are shaped to cooperatively focus a wireless transmission between the cartridge antenna and the channel antenna in the assembled configuration.

Example 32—The surgical instrument of any of Examples 31, further comprising an insulative layer deposed between the longitudinal channel and the channel antenna.

Example 33—The surgical instrument of Example 21, wherein the aligner comprises a first interlocking component at least partially extending around the channel antenna, and a second interlocking component at least partially extending around the cartridge antenna, wherein the second interlocking component and the first interlocking component cooperatively maintain the predefined spatial relation between the channel antenna and the cartridge antenna in the assembled configuration.

Example 34—The surgical instrument of Example 33, wherein the first interlocking component comprises a slot, and the second interlocking component comprises a tab to be received in the slot in the assembled configuration.

Example 35—The surgical instrument of Example 33, wherein the cartridge body comprises a cartridge cavity, and wherein the cartridge antenna is positioned in the cartridge cavity.

Example 36—The surgical instrument of Example 35, wherein the longitudinal channel comprises a channel cavity, wherein the channel antenna is positioned inside the channel cavity, and wherein the channel cavity and the cartridge cavity are shaped to cooperatively focus a wireless transmission between the cartridge antenna and the channel antenna in the assembled configuration.

The present disclosure can be described in the context of staples removably stored within staple cartridges for use with surgical stapling instruments. Staples can include wires which are deformed when they contact an anvil of the surgical stapler. Such wires can be comprised of metal, such as stainless steel, for example, and/or any other suitable material. Such disclosure, and the teachings thereof, can be applied to fasteners removably stored with fastener cartridges for use with any suitable fastening instrument.

The present disclosure can be described in the context of linear end effectors and/or linear fastener cartridges. Such disclosure, and the teachings thereof, can be applied to non-linear end effectors and/or non-linear fastener cartridges, such as, for example, circular and/or contoured end effectors. For example, various end effectors, including non-linear end effectors, are disclosed in U.S. patent application Ser. No. 13/036,647, filed Feb. 28, 2011, entitled SURGICAL STAPLING INSTRUMENT, now U.S. Pat. No. 8,561,870, which is hereby incorporated by reference in its entirety. Additionally, U.S. patent application Ser. No. 12/893,461, filed Sep. 29, 2012, entitled STAPLE CARTRIDGE, now U.S. Pat. No. 8,733,613, is hereby incorporated by reference in its entirety. U.S. patent application Ser. No. 12/031,873, filed Feb. 15, 2008, entitled END EFFECTORS FOR A SURGICAL CUTTING AND STAPLING INSTRUMENT, now U.S. Pat. No. 7,980,443, is also hereby incorporated by reference in its entirety. U.S. Pat. No. 8,393,514, entitled SELECTIVELY ORIENTABLE IMPLANTABLE FASTENER CARTRIDGE, which issued on Mar. 12, 2013, is also hereby incorporated by reference in its entirety. One skilled in the art will recognize that the herein described components (e.g., operations), devices, objects, and the discussion accompanying them are used as examples for the sake of conceptual clarity and that various configuration modifications are contemplated. Consequently, as used herein, the specific examples set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. The instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" or "control system" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the present disclosure has been presented for purposes of illustration and description. It is not intended to be exhaustive or limiting to the precise form disclosed. Modifications or variations are possible in light of the above teachings. The present disclosure illustrates principles and practical application to thereby enable one of ordinary skill in the art to utilize the various embodiments and with various modifications as are suited to the particular use contemplated. It is intended that the claims submitted herewith define the overall scope.

It is worthy to note that any reference numbers included in the appended claims are used to reference exemplary embodiments/elements described in the present disclosure. Accordingly, any such reference numbers are not meant to limit the scope of the subject matter recited in the appended claims.

What is claimed is:

1. A surgical instrument comprising:
a shaft; and
an end effector extending from the shaft, the end effector comprising:
a staple cartridge comprising:
a cartridge deck;
a cartridge body; and
a cartridge antenna supported by the cartridge body
a longitudinal channel comprising:
a base;
a first wall extending from the base;
a second wall extending from the base, wherein the second wall is spaced apart from the first wall to accommodate the staple cartridge therebetween in an assembled configuration; and
a channel antenna supported by the first wall, wherein the cartridge antenna and the channel antenna are to cooperatively define a wireless signal-transfer circuit in the assembled configuration; and
an aligner to interlock the staple cartridge and the longitudinal channel in the assembled configuration, wherein the aligner is adjacent the channel antenna and the cartridge antenna to maintain a predefined spatial relation between the channel antenna and the cartridge antenna in the assembled configuration.

2. The surgical instrument of claim 1, wherein maintaining the predefined spatial relation comprises:
a translational misalignment tolerance of less than or equal to a predefined distance; and
an angular misalignment tolerance of less than or equal to a predefined angle.

3. The surgical instrument of claim 2, wherein the aligner resists a longitudinal sliding of the staple cartridge relative to the longitudinal channel in the assembled configuration.

4. The surgical instrument of claim 2, wherein the aligner resists a vertical sliding of the staple cartridge relative to the longitudinal channel in the assembled configuration.

5. The surgical instrument of claim 2, wherein the aligner is positioned at or below a maximum predefined distance from the wireless signal-transfer circuit in the assembled configuration.

6. The surgical instrument of claim 5, wherein the maximum predefined distance is selected from a range of about 1 mm to about 60 mm.

7. The surgical instrument of claim 5, wherein the maximum predefined distance is selected from a range of about 10 mm to about 20 mm.

8. The surgical instrument of claim 1, further comprising:
an articulation joint assembly extending between the shaft and the end effector; and
a wiring harness to transmit at least one of data or power through the articulation joint assembly, wherein the at least one of data or power is to be wirelessly transmitted between the cartridge antenna and the channel antenna in the assembled configuration.

9. The surgical instrument of claim 8, further comprising a ferrite layer deposed between the cartridge body and the cartridge antenna.

10. The surgical instrument of claim 9, wherein the wiring harness comprises a twisted wire trace pattern.

11. The surgical instrument of claim 2, wherein the aligner comprises:
a first interlocking component at least partially extending around the channel antenna; and
a second interlocking component at least partially extending around the cartridge antenna, wherein the second interlocking component and the first interlocking component cooperatively maintain the predefined spatial relation between the channel antenna and the cartridge antenna in the assembled configuration.

12. The surgical instrument of claim 11, wherein the first interlocking component comprises a slot, and the second interlocking component comprises a tab to be received in the slot in the assembled configuration.

13. The surgical instrument of claim 1, wherein the cartridge body comprises a cartridge cavity, and wherein the cartridge antenna is positioned in the cartridge cavity.

14. The surgical instrument of claim 13, wherein the longitudinal channel comprises a channel cavity, and wherein the channel antenna is positioned inside the channel cavity.

15. The surgical instrument of claim 14, wherein the channel cavity and the cartridge cavity are shaped to cooperatively focus a wireless transmission between the cartridge antenna and the channel antenna in the assembled configuration.

16. The surgical instrument of claim 15, further comprising an insulative layer deposed between the longitudinal channel and the channel antenna.

17. The surgical instrument of claim 5, wherein the aligner comprises:
a first interlocking component at least partially extending around the channel antenna; and
a second interlocking component at least partially extending around the cartridge antenna, wherein the second interlocking component and the first interlocking component cooperatively maintain the predefined spatial relation between the channel antenna and the cartridge antenna in the assembled configuration.

18. The surgical instrument of claim 17, wherein the first interlocking component comprises a slot, and the second interlocking component comprises a tab to be received in the slot in the assembled configuration.

19. The surgical instrument of claim 17, wherein the cartridge body comprises a cartridge cavity, and wherein the cartridge antenna is positioned in the cartridge cavity.

20. The surgical instrument of claim 19, wherein the longitudinal channel comprises a channel cavity, wherein the channel antenna is positioned inside the channel cavity, and wherein the channel cavity and the cartridge cavity are shaped to cooperatively focus a wireless transmission between the cartridge antenna and the channel antenna in the assembled configuration.

* * * * *